United States Patent
Thompson, III et al.

(10) Patent No.: US 9,187,506 B2
(45) Date of Patent: Nov. 17, 2015

(54) (R)-3-((3S,4S)-3-FLUORO-4-(4-HYDROXYPHENYL)PIPERIDIN-1-YL)-1-(4-METHYLBENZYL)PYRROLIDIN-2-ONE AND ITS PRODRUGS FOR THE TREATMENT OF PSYCHIATRIC DISORDERS

(71) Applicant: Bristol-Meyers Squibb Company, Princeton, NJ (US)

(72) Inventors: Lorin A. Thompson, III, Higganum, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/591,372

(22) Filed: Jan. 7, 2015

(65) Prior Publication Data

US 2015/0191496 A1  Jul. 9, 2015

Related U.S. Application Data

(60) Provisional application No. 61/925,405, filed on Jan. 9, 2014.

(51) Int. Cl.
- *A61K 31/5355* (2006.01)
- *C07D 417/14* (2006.01)
- *C07F 9/59* (2006.01)
- *C07D 401/04* (2006.01)

(52) U.S. Cl.
CPC ............... *C07F 9/59* (2013.01); *C07D 401/04* (2013.01)

(58) Field of Classification Search
None
See application file for complete search history.

(56) References Cited

U.S. PATENT DOCUMENTS 7,994,166 B2 * 8/2011 Stamos et al. ............. 514/236.8

FOREIGN PATENT DOCUMENTS

| EP | 1 988 077 A1 | 11/2008 |
|---|---|---|
| WO | WO 01/32615 | 5/2001 |
| WO | WO 01/81295 | 11/2001 |
| WO | WO 03/035641 | 5/2003 |
| WO | WO 2005/035523 | 4/2005 |

OTHER PUBLICATIONS

King et al., U.S. Appl. No. 14/589,205, filed Jan. 5, 2015.
CAS Registry No. 1385072-30-9, Entered STN: Aug. 1, 2012.
CAS Registry No. 1623322-96-2, Entered STN: Sep. 18, 2014.

* cited by examiner

*Primary Examiner* — Timothy R Rozof
(74) *Attorney, Agent, or Firm* — James Epperson

(57) ABSTRACT

The disclosure generally relates to compounds of formula I, including their salts, as well as compositions and methods of using the compounds. The compounds are ligands for the NR2B NMDA receptor and may be useful for the treatment of various disorders of the central nervous system.

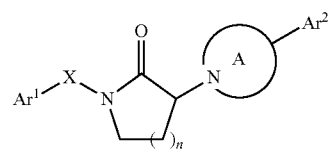

12 Claims, No Drawings

(R)-3-((3S,4S)-3-FLUORO-4-(4-HYDROXYPHENYL)PIPERIDIN-1-YL)-1-(4-METHYLBENZYL)PYRROLIDIN-2-ONE AND ITS PRODRUGS FOR THE TREATMENT OF PSYCHIATRIC DISORDERS

CROSS-REFERENCE TO RELATED APPLICATIONS

This application claims priority to Provisional Patent Application U.S. Ser. No. 61/925,405 filed Jan. 9, 2014, hereby incorporated by reference in its entirety.

BACKGROUND OF THE INVENTION

The disclosure generally relates to compounds of formula I, including their salts, as well as compositions and methods of using the compounds. The compounds are ligands for the NR2B NMDA receptor and may be useful for the treatment of various disorders of the central nervous system.

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists or allosteric modulators of NMDA receptors, in particular NR2B subunit-containing channels, have been investigated as therapeutic agents for the treatment of major depressive disorder (G. Sanacora, 2008, Nature Rev. Drug Disc. 7: 426-437).

The NR2B receptor contains additional ligand binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class of drugs, though, has limited therapeutic value because of its CNS side effects, including dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been hindered by low bioavailability, poor pharmacokinetics, and lack of selectivity against other pharmacological targets including the hERG ion channel. Blockade of the hERG ion channel can lead to cardiac arrythmias, including the potentially fatal Torsades de pointe, thus selectivity against this channel is critical. Thus, in the treatment of major depressive disorder, there remains an unmet clinical need for the development of effective NR2B-selective negative allosteric modulators which have a favorable tolerability profile.

NR2B receptor antagonists have been disclosed in PCT publication WO 2009/006437.

The invention provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

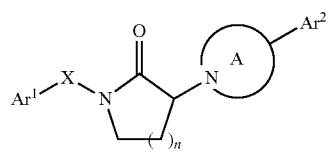

where:
$Ar^1$ is phenyl or indanyl and is substituted with 0-3 substituents selected from cyano, halo, alkyl, haloalkyl, and haloalkoxy;
$Ar^2$ is phenyl substituted with 1 OR substituent and also substituted with 0-3 substituents selected from cyano, halo, alkyl, haloalkyl, and haloalkoxy;
R is a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2; and
ring A is azetidinyl, pyrrolidinyl, piperidinyl, piperazinyl, homopiperidinyl, or homopiperazinyl and is substituted with 0-4 substituents selected from halo, alkyl, hydroxy, or alkoxy; or a pharmaceutically acceptable salt thereof.

Another aspect of the invention is a compound of the formula

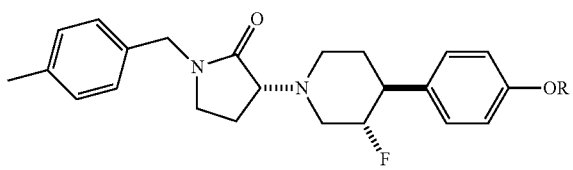

where R is a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates; or a pharmaceutically acceptable salt thereof.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Scheme 1 shows an effective synthesis of example 1, (R)-3-((3S,4S)-3-fluoro-4-(4-hydroxyphenyl)piperidin-1-yl)-1-(4-methylbenzyl)pyrrolidin-2-one. Hydroxylactam 1 is available commercially in optically pure form. It can be protected and N-alkylated to form lactam 4. Deprotection and activation of the hydroxyl group with methanesulfonylchloride leads to the lactam 5. Separately, compound 6 can be prepared by the Suzuki coupling reaction between commercial 4-benzyloxybromobenzene and commercial tert-butyl 4-(4,4,5,5-tetramethyl-1,3,2-dioxaborolan-2-yl)-5,6-dihydropyridine-1(2H)-carboxylate. Treatment of 6 with in-situ prepared borane followed by oxidation results in formation of the trans racemic alcohol 7. The alcohol 7 can be separated in to the individual enantiomers, and the phenol can be unmasked using hydrogenation under standard conditions to the prepare the substituted phenol 8. Fluorination with de-oxofluor reagent provides selectively the trans aryl fluoride 9, and deprotection of the Boc group with hydrochloric acid provides the piperidine as the hydrochloride salt. Simple extraction under basic conditions provides the piperidine 10 as the freebase. Careful reaction of the piperidine 10 with the lactam 5 under mildly basic conditions provides (R)-3-((3S,4S)-3-fluoro-4-(4-hydroxyphenyl)piperidin-1-yl)-1-(4-methylbenzyl)pyrrolidin-2-one, the title compound of example 1.

Scheme 1. Synthesis of (R)-3-((3S,4S)-3-fluoro-4-(4-hydroxyphenyl)piperidin-1-yl)-1-(4-methylbenzyl)pyrrolidin-2-one

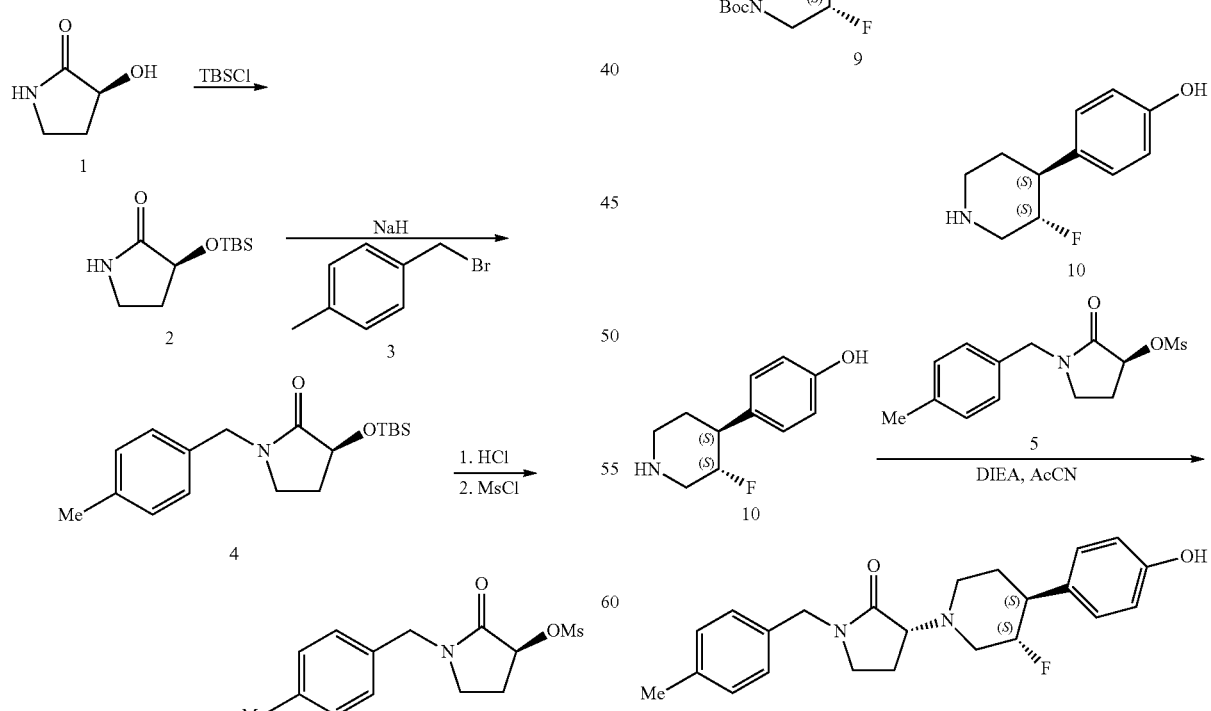

Example 1

The compound of example 1 can be transformed into a variety of prodrugs using methods known in the art. Thus, according to scheme 2, treatment of the phenol with POCl₃, pyridine, and DMAP followed by aqueous hydrolysis provides example 2, the dihydrogen phosphate ester of example 1.

Scheme 2. Synthesis of example 2, the phosphonic acid prodrug of the compound of example 1

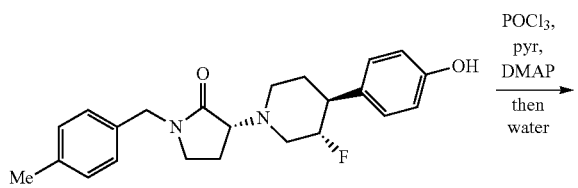

Example 1

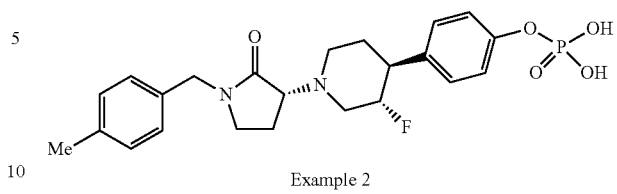

Example 2

Similarly, reaction of the compound of example 1 with a Boc-protected amino acid using a variety of methods known in the art, but preferably using dicyclohexylcarbodiimide and 4-dimethylaminopyridine provides the ester 11. Clevage of the Boc group in acid, preferably HCl, provides the esters which include the compounds of examples 3 and 4.

Scheme 3. Synthesis of Amino Acid Prodrugs

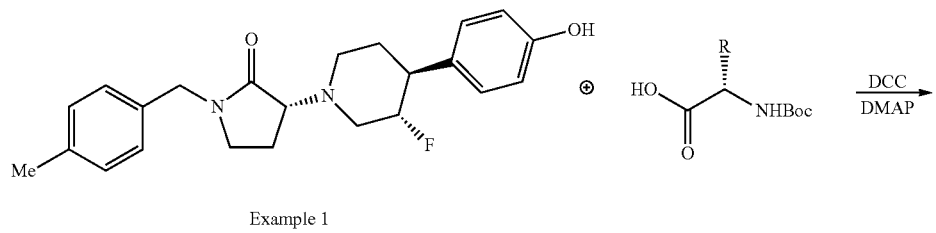

Example 1

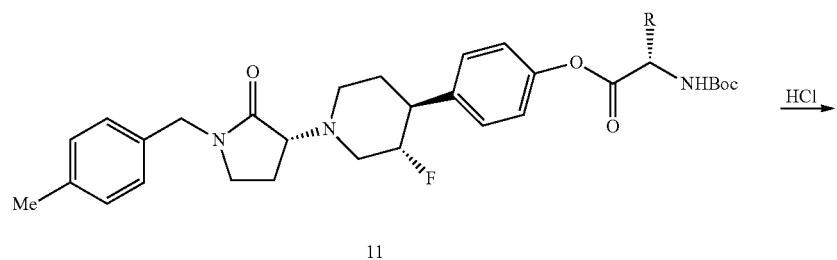

11

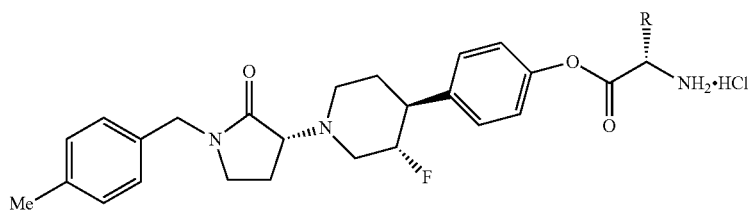

Examples 3, 4

In a similar manner, Boc-protected aspartic acid tert-butyl ester (12) can be coupled through the unprotected sidechain to the compound of example 1 to provide the ester 13. Deprotection with HCl again provides the compound of example 5.

Scheme 4. Synthesis of Aspartic Acid Prodrug with Attachment Through the Sidechain Carboxylic Acid

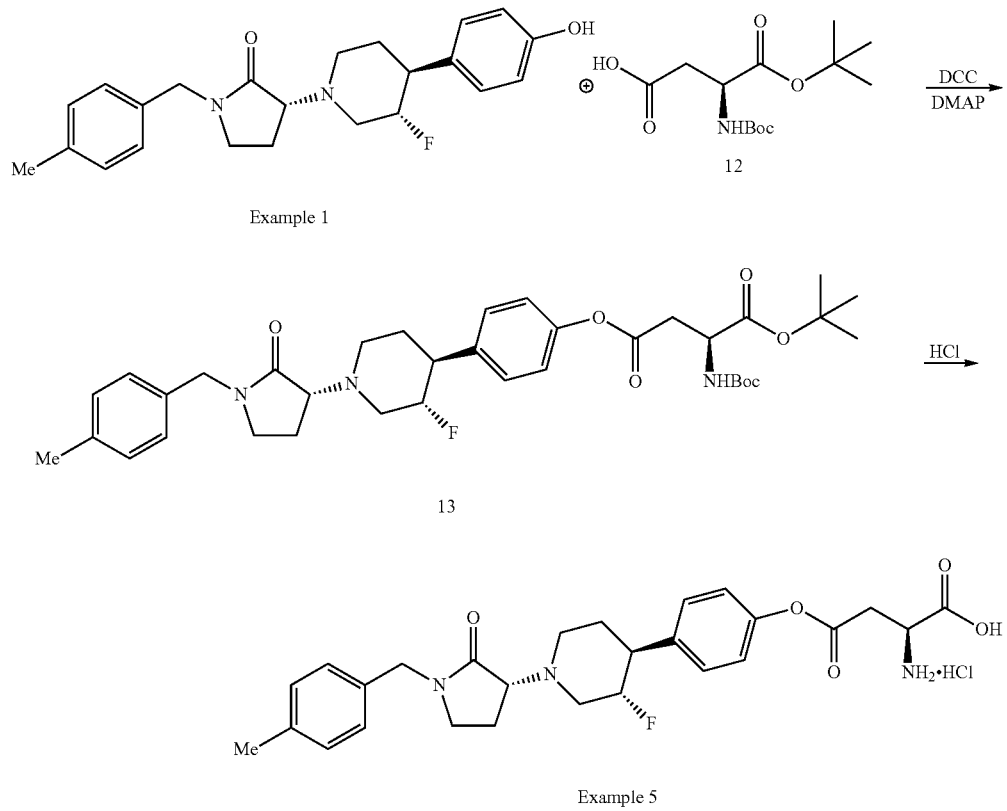

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "satd." for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "DCM" for dichloromethane, "TLC" or "tlc" for thin layer chromatography, "SFC" for supercritical fluid chromatography, "NMR" for nuclear magnetic resonance spectroscopy, "$^1$H" for proton, " " for delta, "s" for singlet, "d" for doublet, "t" for triplet, "q" for quartet, "m" for multiplet, "br" for broad, "Hz" for hertz, and "R", "S", "E", and "Z" are stereochemical designations familiar to one skilled in the art.

LC/MS data were acquired using the following conditions:

Conditions A: Ascentis C18 50×2.1 mm, 2.7 µm column using a 1 mL/min flowrate gradient of 0-100% B over 1.7 minutes followed by 1.3 minutes at 100% B. Solvent A: 10 mM NH4COOH in water:acetonitrile (98:2); solvent B=10 mM NH4COOH in water:acetonitrile (2:98).

Conditions B: Phenomenex C18 2.0×50 mm, 5 µm column using a 0.8 mL/min flowrate gradient of 0-100% B over 4 minutes. Solvent A=10% MeOH/90% water/0.1% TFA, Solvent B=90% MeOH/10% water/0.1% TFA.

Synthesis of Intermediates

Intermediate A. tert-Butyl 4-(4-(benzyloxy)phenyl)-5,6-dihydropyridine-1(2H)-carboxylate

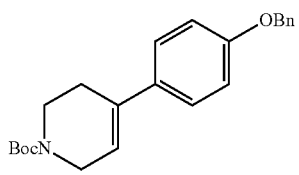 [SMILES: CC(C)(C)OC(=O)N1CC=C(c2ccc(OCc3ccccc3)cc2)CC1]

A solution of commercial 1-(benzyloxy)-4-bromobenzene (104 g, 395 mmol) and commercial tert-butyl 4-(4,4,5,5-tetramethyl-1,3,2-dioxaborolan-2-yl)-5,6-dihydropyridine-1(2H)-carboxylate (147 g, 474 mmol) in 1100 mL of acetonitrile was purged with nitrogen for 2 min. Water (1100 mL) was added, followed by sodium carbonate (126 g, 1186 mmol) and tetrakis(triphenylphosphine)palladium (27.4 g, 23.7 mmol). The reaction mixture was purged with nitrogen for 5 min, and then heated to 90° C. and stirred for 16 h. The reaction mixture was then allowed to cool to rt and diluted with 1 L of ethyl acetate. The layers were separated, and the aqueous layer was extracted with two additional 250 mL portions of ethyl acetate. The organic layers were combined, washed with 200 mL of brine, dried over sodium sulfate, and evaporated in vacuo to provide an off-white solid. The product was purified by silica gel chromatography eluting with 6% ethyl acetate in petroleum ether to provide 129 g (88%) of the desired product. LC/MS RT (conditions A)=2.732 min, (M−H)+=364.0. $^1$H NMR (300 MHz, chloroform-d) δ 7.49-7.30 (m, 5H), 7.27 (d, J=10.7 Hz, 2H), 6.99-6.87 (m, 2H), 6.03-5.87 (m, 1H), 5.07 (s, 2H), 4.05 (d, J=2.6 Hz, 2H), 3.62 (t, J=5.7 Hz, 2H), 2.49 (br. s., 2H), 1.49 (s, 9H).

Intermediate B. (+/−)-rel-(3S,4S)-tert-Butyl 4-(4-(benzyloxy)phenyl)-3-hydroxypiperidine-1-carboxylate

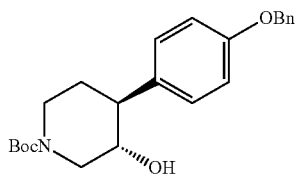 [SMILES: CC(C)(C)OC(=O)N1CC[C@@H](c2ccc(OCc3ccccc3)cc2)[C@H](O)C1]

Sodium borohydride (15.5 g, 410 mmol) was dissolved in THF, and the solution was chilled to 0° C. Boron trifluoride etherate (52.3 mL, 424 mmol) was added to the solution and the mixture was allowed to warm to rt and stirred for 30 min. Then a solution of tert-butyl 4-(4-(benzyloxy)phenyl)-5,6-dihydropyridine-1(2H)-carboxylate (50 g, 137 mmol, intermediate A) in 500 mL of THF was added and the reaction mixture was stirred for 2 h at rt. A 100 mL portion of water was then added slowly to the mixture (Caution: effervescence is observed). The mixture was diluted with 100 mL of ethanol, and sodium hydroxide (228 mL, 10% solution in water, 0.684 mol) and hydrogen peroxide (20.5 mL, 0.684 mol) were added. The reaction mixture was heated to reflux temperature and stirred for 16 h. The mixture was cooled to 10° C. and diluted with 1 L of DCM. Then the pH was adjusted to 7 with 1.5 L of 1.5 N HCl. The layers were then separated, and the aqueous layer was extracted with an addition two 500 mL portions of DCM. The organic layers were combined, washed with 2×1 L of water and 200 mL of brine, dried over sodium sulfate, and evaporated in vacuo to provide an off-white solid. The solid was triturated with 500 mL of pet ether, and isolated by filtration to yield 46.5 grams of product (88%, 99.0% purity by HPLC). LC/MS RT (conditions A)=2.372 min, (M+H)+=382.0. $^1$H NMR (400 MHz, DMSO-$d_6$) δ 7.47-7.42 (m, 2H), 7.42-7.36 (m, 2H), 7.36-7.28 (m, 1H), 7.14 (d, J=9.0 Hz, 2H), 6.92 (d, J=9.0 Hz, 2H), 5.07 (s, 2H), 4.74 (d, J=5.5 Hz, 1H), 4.10 (br. s., 1H), 3.94 (br. s., 1H), 3.46-3.35 (m, 1H), 2.47-2.31 (m, 2H), 1.70-1.61 (m, 1H), 1.55-1.45 (m, 2H), 1.42 (s, 9H).

Intermediate C. (3S,4S)-tert-Butyl 4-(4-(benzyloxy)phenyl)-3-hydroxypiperidine-1-carboxylate

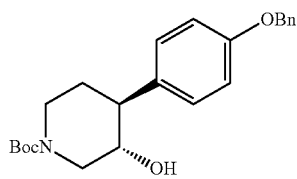 [SMILES: CC(C)(C)OC(=O)N1CC[C@@H](c2ccc(OCc3ccccc3)cc2)[C@H](O)C1]

Racemic rel-(3S,4S)-tert-butyl 4-(4-(benzyloxy)phenyl)-3-hydroxypiperidine-1-carboxylate (112 g, intermediate B) was separated into the individual enantiomers using preparative supercritical fluid chromatography under the following conditions: A Thar SFC-250 instrument was utilized with a Lux-Cellulose-2 (250×21 mm), 5 μm column eluting with 60% $CO_2$ and 40% of a solution of 0.3% diethylamine in methanol at a flow rate of 100.0 g/min. Sample was injected at 74 mg/mL. Analytical SFC was carried out on Lux-Cellulose-2 (250×4.6 mm), 5 μm column eluting with 55% $CO_2$ and 45% of a solution of 0.3% diethylamine in methanol at a flow rate of 3.0 g/min. The recovery was 50.0 g of peak 1 with a retention time of 2.49 minutes, which corresponds to the desired (3S,4S)-tert-butyl 4-(4-(benzyloxy)phenyl)-3-hydroxypiperidine-1-carboxylate. Analytical data matched those from the racemate.

Intermediate D. (3S,4S)-tert-Butyl 3-hydroxy-4-(4-hydroxyphenyl)piperidine-1-carboxylate

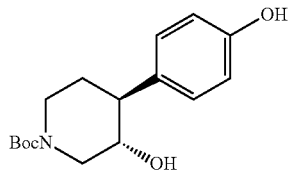 [SMILES: CC(C)(C)OC(=O)N1CC[C@@H](c2ccc(O)cc2)[C@H](O)C1]

A solution of (3S,4S)-tert-butyl 4-(4-(benzyloxy)phenyl)-3-hydroxypiperidine-1-carboxylate (26 g, 67.8 mmol, intermediate C) in 260 mL of methanol was treated with 1.6 grams of 10% palladium on carbon (13.6 mmol) in a pressure bottle. Hydrogen at 50 psi was introduced, and the reaction mixture was stirred for 16 h.

The mixture was filtered through celite and concentrated to a crude product (18.9 g, 64.4 mmol) which was sufficiently pure to carry forward without further purification. LC/MS RT (conditions B)=2.970 min, (M+H with loss of t-butyl)⁺=238.0. ¹H NMR (400 MHz, DMSO-d₆) δ 9.10 (br. s., 1H), 7.01 (d, J=8.5 Hz, 2H), 6.65 (s, 2H), 4.70 (d, J=5.0 Hz, 1H), 4.09 (br. s., 1H), 3.93 (br. s., 1H), 3.17 (s, 2H), 2.79-2.63 (m, 1H), 2.34 (br. s., 1H), 1.68-1.57 (m, 1H), 1.44 (br. s., 1H), 1.42 (s, 9H).

Intermediate E. (3S,4S)-tert-Butyl 3-fluoro-4-(4-hydroxyphenyl)piperidine-1-carboxylate

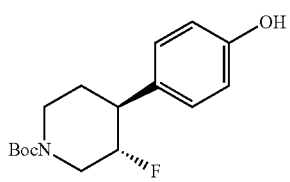 [SMILES: CC(C)(C)OC(=O)N1CC[C@@H](c2ccc(O)cc2)[C@H](F)C1]

A solution of (3S,4S)-tert-butyl 3-hydroxy-4-(4-hydroxyphenyl)piperidine-1-carboxylate (15.5 g, 61.4 mmol, intermediate D) in 270 mL of acetonitrile was chilled to 0° C. To the stirred solution was added bis(2-methoxyethyl)aminosulfur trifluoride 50% solution in toluene (Deoxo-fluor, 58.4 mL, 159 mmol) dropwise via addition funnel over 65 min. After the addition, the reaction mixture was stirred for 30 min at 0° C. and then allowed to come to rt and stirred for an additional 2 h. A saturated ammonium chloride solution (150 mL) was then added, and the mixture was extracted with two 150 mL portions of DCM. The organic layers were combined, dried over sodium sulfate, and concentrated to afford the crude product. The product was purified by silica gel chromatography (1.5 kg of silica) eluting with a gradient of 0-15% acetone in hexanes to afford 11.9 g (75%) of the desired (3S,4S)-tert-butyl 3-fluoro-4-(4-hydroxyphenyl)piperidine-1-carboxylate. LC/MS RT (conditions B)=3.295 min, (M+H with loss of t-butyl and elimination of fluorine)⁺=220.0. ¹H NMR (400 MHz, chloroform-d) δ 7.15 (d, J=8.6 Hz, 2H), 6.83 (dt, J=8.6, 2.0 Hz, 2H), 4.59-4.48 (m, 1H), 4.47-4.37 (m, 1H), 4.23-4.12 (m, 1H), 2.88-2.68 (m, 3H), 1.96-1.84 (m, 1H), 1.80-1.66 (m, 1H), 1.51 (s, 9H).

Intermediate F.
4-((3S,4S)-3-Fluoropiperidin-4-yl)phenol

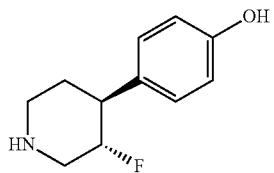 [SMILES: Oc1ccc([C@@H]2CCNC[C@H]2F)cc1]

A solution of (3S,4S)-tert-butyl 3-fluoro-4-(4-hydroxyphenyl)piperidine-1-carboxylate (12.0 g, 40.6 mmol, intermediate E) in anhydrous dioxane (80 mL) was treated with HCl (4 M in 1,4-dioxane, 40.6 mL, 162 mmol). The reaction mixture was allowed to stir at rt for 6 h and then evaporated in vacuo to provide the HCl salt of the desired product. Without further isolation, the HCl salt was suspended in CHCl₃ and 80 mL of a satd. NaHCO₃ solution was added. The organic layer was separated, and the aqueous layer was extracted with CHCl₃ (2×100 mL). The organic layers were combined, dried over Na₂SO₄ and concentrated to give the title compound (7.1 g, 36.4 mmol, 90%). LC/MS RT (conditions B)=1.008 min, LC/MS (M+H)⁺=196.2.

Intermediate G. (S)-3-((tert-Butyldimethylsilyl)oxy)pyrrolidin-2-one

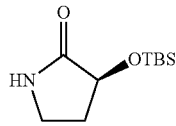

A stirred solution of commercial (S)-3-hydroxypyrrolidin-2-one (5 g, 49.5 mmol) in DCM (198 ml) was treated with DMAP (0.199 g, 1.632 mmol), imidazole (6.73 g, 99 mmol), and TBDMS-Cl (8.94 g, 59.3 mmol). The reaction mixture was stirred at rt for 16 h, and then was washed with a satd. NaHCO₃ solution. The organic layer was concentrated and the crude reaction product was purified by silica gel chromatogpraphy eluting with 50% ethyl acetate in petroleum ether. The desired product was isolated as a white solid (8.1 g, 76%). LC/MS (M+H)⁺=216.2. ¹H NMR (400 MHz, chloroform-d) δ 6.40 (br. s., 1H), 4.26 (t, J=7.8 Hz, 1H), 3.42-3.34 (m, 1H), 3.29-3.21 (m, 1H), 2.36 (dtd, J=12.7, 7.3, 3.3 Hz, 1H), 2.07-1.96 (m, 1H), 0.91 (s, 9H), 0.15 (d, J=7.0 Hz, 6H).

Intermediate H. (S)-3-((tert-Butyldimethylsilyl)oxy)-1-(4-methylbenzyl)pyrrolidin-2-one

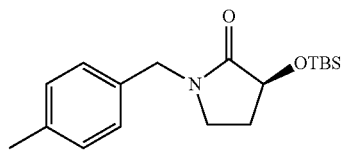 [SMILES: Cc1ccc(CN2CC[C@H](O[Si](C)(C)C(C)(C)C)C2=O)cc1]

(S)-3-((tert-butyldimethylsilyl)oxy)pyrrolidin-2-one (5 g, 23.22 mmol, intermediate G) was dissolved in anhydrous THF (46.4 ml) and the reaction mixture was cooled to 0° C. under a nitrogen atmosphere. Sodium hydride (1.393 g, 34.8 mmol) was then added in one portion and the reaction mixture was allowed to stir for 5 min before the dropwise addition of 1-(bromomethyl)-4-methylbenzene (5.37 g, 29.0 mmol) in anhydrous THF (46.4 ml). The reaction was allowed to stir at 0° C. for 5 min, then the cooling bath was removed and mixture was allowed to warm to rt overnight. The reaction was cautiously quenched with water (100 mL) and then extracted with ethyl acetate (3×100 mL). The combined organic layers were then washed with brine (200 mL) and dried (MgSO₄). Evaporation of the solvent in vacuo gave the crude product (9.6 g, oil) which was then purified by silica gel chromatography (330 g of silica) eluting with a gradient of 0% to 20% ethyl acetate in hexanes to provide 6.53 g (88%) of the desired product. LC/MS (Conditions B), RT=4.320 min, (M+H)⁺=320.3. ¹H NMR (400 MHz, chloroform-d) δ 7.15 (s, 4H), 4.42 (s, 2H), 4.37 (t, J=7.6 Hz, 1H), 3.32-3.18

(m, 1H), 3.10 (dt, J=9.7, 7.5 Hz, 1H), 2.36 (s, 3H), 2.29 (dtd, J=12.6, 7.6, 3.1 Hz, 1H), 1.97-1.84 (m, 1H), 0.95 (s, 9H), 0.20 (d, J=10.3 Hz, 6H).

Intermediate I. (S)-3-Hydroxy-1-(4-methylbenzyl)pyrrolidin-2-one

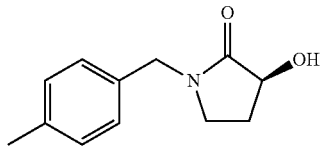

HCl (4 M in 1,4-dioxane, 25.5 ml, 102 mmol) was added in one portion to a solution of (S)-3-((tert-butyldimethylsilyl)oxy)-1-(4-methylbenzyl)pyrrolidin-2-one (6.53 g, 20.44 mmol, intermediate H) in anyhdrous DCM (20.4 mL) at rt. A slight exotherm was noted. The reaction mixture was allowed to stir at rt for 2 h and then evaporated in vacuo. The residue was taken up in DCM (100 mL) and washed with a satd. sodium bicarbonate solution (100 mL) and brine (50 mL), and then the solution was dried over MgSO$_4$ and concentrated to a residue. The crude product was purified by silica gel chromatography (120 g of silica) eluting with a gradient of 40% to 100% ethyl acetate in hexanes to provide 3.73 g (89%) of the desired product. LC/MS (Conditions B), RT=2.338 min, (M+H)$^+$=206.2. $^1$H NMR (400 MHz, chloroform-d) δ 7.26-7.02 (m, 4H), 4.43 (d, J=3.5 Hz, 2H), 4.41-4.37 (m, 1H), 3.66 (d, J=2.6 Hz, 1H), 3.34-3.05 (m, 2H), 2.41 (dddd, J=12.8, 8.4, 6.6, 2.2 Hz, 1H), 2.34 (s, 3H), 1.93 (dq, J=12.8, 8.8 Hz, 1H).

Intermediate J. (S)-1-(4-methylbenzyl)-2-oxopyrrolidin-3-yl methanesulfonate

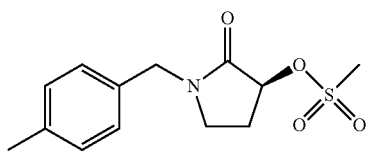 [SMILES: Cc1ccc(CN2CC[C@H](OS(C)(=O)=O)C2=O)cc1]

Triethylamine (0.509 ml, 3.65 mmol) was added to a cooled solution of (S)-3-hydroxy-1-(4-methylbenzyl)pyrrolidin-2-one (0.5 g, 2.436 mmol, intermediate I) in anhydrous DCM (12.18 ml) at 0° C. under a nitrogen atmosphere. Methanesulfonyl chloride (0.198 ml, 2.56 mmol) was then added dropwise and the reaction was allowed to stir at 0° C. for 15 min before quenching with a satd. sodium bicarbonate solution (10 mL). The mixture was allowed to warm to rt and the aqueous layer was separated and extracted with DCM (2×). The combined organic layers were dried over MgSO$_4$ and evaporated in vacuo to give a white solid (0.73 g) which was then purified by silica gel chromatography (40 g of silica) eluting with a gradient of 0% to 50% ethyl acetate in hexanes to provide 0.63 g (91%) of the desired product as a white solid.

Intermediate K. (S)-3-(tert-Butyldimethylsilyloxy)-1-(4-(difluoromethyl)benzyl)pyrrolidin-2-one

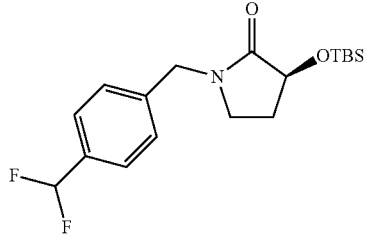 [SMILES: CC(C)(C)[Si](C)(C)O[C@H]1CCN(Cc2ccc(C(F)F)cc2)C1=O]

A 60% dispersion of sodium hydride in mineral oil (232 mg, 5.31 mmol) was added to a stirred solution of (S)-3-((tert-butyldimethylsilyl)oxy)pyrrolidin-2-one (762 mg, 3.54 mmol, intermediate G) in THF (7 mL) at 0° C. After 15 min, a solution of 1-(bromomethyl)-4-(difluoromethyl)benzene (980 mg, 4.43 mmol) in THF (7 mL) was added to the reaction mixture. The resulting mixture was stirred at room temperature for 6 h. The reaction was carefully quenched with several grams of ice pellets. The resulting mixture was extracted with EtOAc. The combined organic layers were washed with water, dried over sodium sulfate, filtered and concentrated in vacuo. The crude reaction mixture was purified using silica gel column chromatography (0-30% EtOAc/hexanes) to afford the desired product (440 mg, 35% yield) as a white solid: LCMS (M+H)$^+$ 356.3; $^1$H NMR (500 MHz, chloroform-d) δ 7.49 (d, J=8.1 Hz, 2H), 7.35 (d, J=7.9 Hz, 2H), 6.65 (br. t, J=1.0 Hz, 1H), 4.56-4.44 (m, 2H), 4.38 (t, J=7.5 Hz, 1H), 3.27 (ddd, J=9.7, 8.7, 3.4 Hz, 1H), 3.13 (dt, J=9.7, 7.4 Hz, 1H), 2.36-2.27 (m, 1H), 1.98-1.90 (m, 1H), 0.96 (br. s., 9H), 0.22-0.20 (m, 3H), 0.20-0.18 (m, 3H).

Intermediate L. (S)-1-(4-(Difluoromethyl)benzyl)-3-hydroxypyrrolidin-2-one

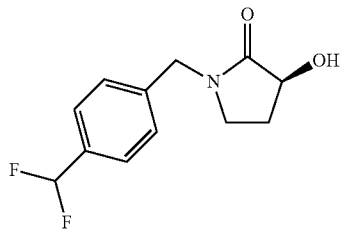 [SMILES: O=C1[C@@H](O)CCN1Cc1ccc(C(F)F)cc1]

A solution of 4 M HCl in dioxane (0.62 mL, 2.5 mmol) was added to a stirred solution of (S)-3-((tert-butyldimethylsilyl)oxy)-1-(4-(difluoromethyl)benzyl)pyrrolidin-2-one (440 mg, 1.24 mmol, intermediate K) in dichloromethane (1.24 mL) at rt. The reaction mixture was stirred for 2 h. The Intermediate M. (S)-1-(4-(Difluoromethyl)benzyl)-2-oxopyrrolidin-3-yl methanesulfonate

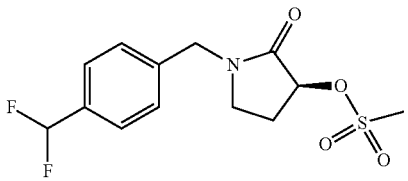 [SMILES: CS(=O)(=O)O[C@H]1CCN(Cc2ccc(C(F)F)cc2)C1=O]

Triethylamine (0.319 mL, 2.29 mmol) and methansulfonyl chloride (0.131 mL, 1.68 mmol) was added to a stirred solution of (S)-1-(4-(difluoromethyl)benzyl)-3-hydroxypyrrolidin-2-one (368 mg, 1.53 mmol, intermediate L) in dichloromethane (7.63 mL) at 0° C. The reaction mixture was stirred at 0° C. for 1 h. The resulting mixture was diluted with water and the aqueous mixture was extracted with dichloromethane. The combined organic layers were washed with 10% sodium bicarbonate solution, dried over sodium sulfate, filtered, and concentrated in vacuo. The crude material was purified using silica gel column chromatography (0-100% EtOAc). The pure fractions were combined and concentrated in vacuo to afford the desired product (322 mg, 66% yield) as a white solid: LC-MS (M+H)$^+$ 320.1; $^1$H NMR (500 MHz, chloroform-d) δ 7.53 (d, J=7.9 Hz, 2H), 7.38-7.33 (m, 2H), 6.67 (br. t, J=1.0 Hz, 1H), 5.27 (dd, J=8.2, 7.5 Hz, 1H), 4.60-4.49 (m, 2H), 3.41-3.35 (m, 1H), 3.33 (s, 3H), 3.27 (dt, J=9.9, 7.3 Hz, 1H), 2.64-2.55 (m, 1H), 2.27 (ddt, J=13.9, 8.9, 7.1 Hz, 1H).

Intermediate N. tert-Butyl 4-hydroxy-4-(4-methoxyphenyl)piperidine-1-carboxylate

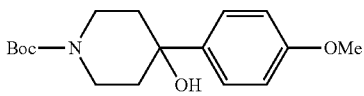 [SMILES: COc1ccc(C2(O)CCN(C(=O)OC(C)(C)C)CC2)cc1]

A mixture of commercial tert-butyl 4-oxopiperidine-1-carboxylate (2.0 g, 10.0 mmol) and diethyl ether (30 ml) was cooled to 0° C. To this mixture was added dropwise a solution of (4-methoxyphenyl)magnesium bromide (0.5 M in diethyl ether, 30 ml, 15 mmol). After complete addition, the reaction mixture was allowed to warm to rt and stirred for 2 h. It was then slowly quenched with 150 ml of ice cold water and then the resulting mixture was extracted with 3×150 ml of DCM. The organic layers were combined, dried, filtered, and concentrated under vacuum. The crude product was purified by silica gel column chromatography (30:70 ethyl acetate:hexane) to provide the desired product (3.0 g, 100% yield): LC-MS (ES-API): m/z 305.5 (M−H)$^+$; $^1$H NMR (400 MHz, DMSO-d$_6$) δ 7.37 (q, J=1.0 Hz, 2H), 6.86 (q, J=1.0 Hz, 2H), 4.94 (s, 1H), 3.82 (d, J=11.5 Hz, 2H), 3.73 (s, 3H), 3.13 (br. s, 2H), 1.75 (td, J=12.9, 4.8 Hz, 2H), 1.56 (d, J=12.3 Hz, 2H), 1.41 (s, 9H).

Intermediate O. 4-(4-Methoxyphenyl)-1,2,3,6-tetrahydropyridine hydrochloride

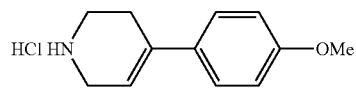

A mixture of tert-butyl 4-hydroxy-4-(4-methoxyphenyl)piperidine-1-carboxylate (700 mg, 2.27 mmol, intermediate N) and HCl in dioxane (4.0 ml, 16 mmol) was stirred at rt for 3 h. The crude mass was concentrated under vacuum and the solid residue was washed with 3×10 ml of DCM to remove non-polar impurities. The desired salt was collected as a fine solid (480 mg, 93%). LCMS (ES-API) m/z 190.2 (M+H)$^+$; $^1$H NMR (400 MHz, DMSO-d$_6$) δ 7.37 (d, J=9.0 Hz, 2H), 6.98 (d, J=9.0 Hz, 2H), 6.08-5.98 (m, 1H), 5.11 (s, 1H), 3.97 (br. s., 1H), 3.52 (s, 1H), 3.32 (s, 3H), 2.47-2.37 (m, 1H).

Intermediate P. 4-(4-Methoxyphenyl)piperidine hydrochloride

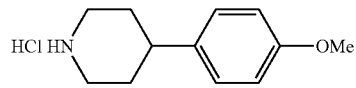

To a stirred solution of 4-(4-methoxyphenyl)-1,2,3,6-tetrahydropyridine, HCl (3.00 g, 13.3 mmol, intermediate O) in methanol (20 mL) was added 10% palladium on carbon (1.4 g) and the reaction mixture was stirred at 20 psi of hydrogen for 12 h. The reaction mixture was filtered through a pad of celite, which was washed with ethyl acetate, and the combined organic fractions were concentrated to obtain a white solid (2.0 g, 70% yield): LCMS (ES-API), m/z 192.1 (M+H)$^+$; $^1$H NMR (300 MHz, DMSO-d$_6$) δ 9.13-8.36 (m, 2H), 7.14 (d, J=8.7 Hz, 2H), 6.90 (d, J=8.7 Hz, 2H), 3.73 (s, 3H), 3.07-2.87 (m, 4H), 2.87-2.65 (m, 4H).

Intermediate Q. 2,4-Dibromo-N-(4-fluorobenzyl)butanamide

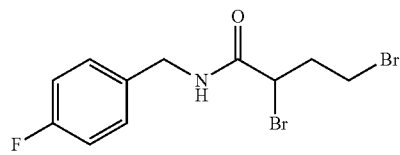 [SMILES: O=C(NCc1ccc(F)cc1)C(Br)CCBr]

TEA (8.91 mL, 63.9 mmol) and 2,4-dibromobutanoyl chloride (5.07 mL, 38.4 mmol) were sequentially added to solution of commercial (4-fluorophenyl)methanamine (4.0 g, 32.0 mmol) in diethyl ether (15 mL) at 0° C. The reaction mixture was allowed to warm to rt and stir for an additional 24 h. The reaction mixture was filtered. The solids were washed with diethyl ether. The filtrate was concentrated in vacuo to afford a crude mixture containing 2,4-dibromo-N-(4-fluorobenzyl)butanamide (8.0 g, 71% yield): LCMS (ES-API), m/z 354, 356 (M+H)+.

Intermediate R.
3-Bromo-1-(4-fluorobenzyl)pyrrolidin-2-one

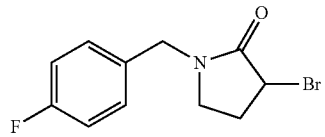 [SMILES: O=C1C(Br)CCN1Cc1ccc(F)cc1]

A 60% dispersion of NaH in mineral oil (1.70 g, 42.5 mmol) was added to a stirred solution of 2,4-dibromo-N-(4-fluorobenzyl)butanamide (10.0 g, 28.3 mmol, intermediate Q) in THF (25 mL) at 0° C. The reaction mixture was allowed to warm to rt and stir for and additional 2 h. The reaction mixture was carefully quenched with ice and diluted with water. The resulting mixture was extracted with EtOAc. The combined organic layers were washed with water and then brine solution. The organic layer was over sodium sulfate, filtered, and concentrated in vacuo. The crude product was purified using silica gel column chromatography (10% EtOAc/hexanes) to afford the desired product (5.90 g, 64% yield): LCMS (ES-API), m/z 272.4, 274.3 (M+H)+; 1H NMR (400 MHz, DMSO-$d_6$) δ ppm 2.12-2.27 (m, 1H) 2.56-2.68 (m, 1H) 3.27 (dd, J=7.78, 3.26 Hz, 2H) 4.29-4.38 (m, 1H) 4.40-4.57 (m, 1H) 4.73 (dd, J=7.03, 3.01 Hz, 1H) 7.04-7.35 (m, 4H).

Intermediate S. 1-(4-Fluorobenzyl)-3-(4-(4-methoxyphenyl)piperidin-1-yl)pyrrolidin-2-one

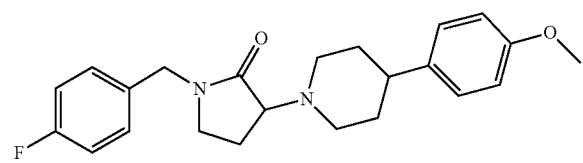 [SMILES: COc1ccc(C2CCN(C3CCN(Cc4ccc(F)cc4)C3=O)CC2)cc1]

TEA (0.768 mL, 5.51 mmol) was added to a stirred solution of 3-bromo-1-(4-fluorobenzyl)pyrrolidin-2-one (0.3 g, 1.10 mmol, intermediate R) and 4-(4-methoxyphenyl)piperidine hydrochloride (0.276 g, 1.213 mmol, intermediate P) in acetonitrile (10 mL). The reaction mixture was sealed and heated in a chemistry microwave at 100° C. for 1 h. The reaction mixture was cooled to rt and concentrated in vacuo. The residue was diluted with EtOAc. The organic mixture was washed with water and brine solution. The organic layer was dried over sodium sulfate, filtered and concentrated in vacuo to afford a crude mixture containing 1-(4-fluorobenzyl)-3-(4-(4-methoxyphenyl)piperidin-1-yl)pyrrolidin-2-one (0.35 g, 83% yield): LCMS (ES-API), m/z 383.2 (M+H)+.

Example 1

(R)-3-((3S,4S)-3-fluoro-4-(4-hydroxyphenyl)piperidin-1-yl)-1-(4-methylbenzyl)pyrrolidin-2-one

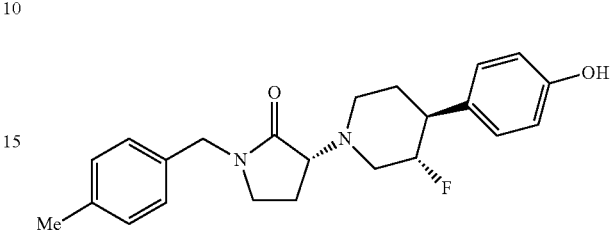

A solution of 4-((3S,4S)-3-fluoropiperidin-4-yl)phenol (7.10 g, 36.4 mmol, intermediate F) and DIEA (16 mL, 92 mmol) in 100 mL of acetonitrile was heated to 80° C. This solution was treated dropwise with a solution of (S)-1-(4-methylbenzyl)-2-oxopyrrolidin-3-yl methanesulfonate (10.5 g, 37.0 mmol, intermediate J) in acetonitrile (80 mL) over a period of 4 hours. After the addition was completed, the reaction mixture was stirred at 80° C. for 16 h. The reaction mixture was then allowed to cool to rt, and the volume was reduced by rotary evaporation to 80 mL. A satd. NH4Cl solution (100 mL) was then added, and the layers were separated. The aqueous layer was extracted with DCM (2×100 mL) and the organic layers were combined, dried over Na2SO4 and concentrated in vacuo to give a crude product. The crude product was purified by silica gel chromatography (750 g of silica gel) eluting with a gradient of 0% to 20% of solvent B in solvent A, where Solvent B=20% methanol/DCM and solvent A=DCM. Fractions containing the product were combined. Evaporation of the solvents gave 9.3 grams of the desired product with 97% purity by LC/MS analysis (conditions B). The product thus obtained (8.5 g) was slurried in acetone:hexane (1:5, 200 mL) and the solid product was isolated by filtration and air dried. Careful SFC analysis showed the presence of a 2.1% impurity in the product. Using a Cel4 0.46×25 cm 5 μm column and eluting with 45% methanol in CO2 at 3 mL/min, the desired product eluted at 3.800 minutes and the undesired impurity eluted at 4.848 minutes. The product was then further purified by SFC Chromatography using a Cel4 3×25 cm 5 μm column at 150 mL/min injecting 1.5 mL of a 80 mg/mL solution. Concentration of the active fractions provided 7.82 grams (20.4 mmol, 56%) of >99.7% pure example 1 as a white powder. LC/MS (Conditions B), RT=2.512 min, (M+H)+=383.3. 19F NMR δ −182.83. 1H NMR (400 MHz, chloroform-d) δ 7.20-7.08 (m, 6H), 6.98-6.78 (m, 2H), 5.68 (s, 1H), 4.77-4.54 (m, 1H), 4.53-4.34 (m, 2H), 3.68 (t, J=8.8 Hz, 1H), 3.41-3.29 (m, 1H), 3.28-3.09 (m, 2H), 2.82 (d, J=10.8 Hz, 1H), 2.74-2.54 (m, 2H), 2.47 (td, J=9.9, 3.6 Hz, 1H), 2.34 (s, 3H), 2.19-1.94 (m, 2H), 1.92-1.80 (m, 2H). 13C NMR (101 MHz, chloroform-d) δ 172.4, 154.9, 137.5, 133.3, 133.0, 129.5, 128.7, 128.3, 115.5, 92.6, 90.8, 65.0, 54.4, 54.2, 48.7, 48.0, 47.8, 46.8, 43.7, 31.7, 31.6, 21.1, 19.6.

Example 2

4-((3S,4S)-3-Fluoro-1-((R)-1-(4-methylbenzyl)-2-oxopyrrolidin-3-yl)piperidin-4-yl)phenyl dihydrogen phosphate

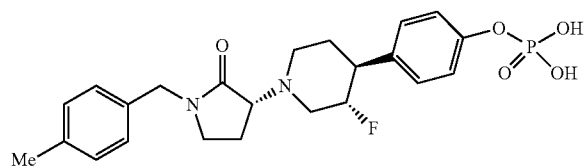 [SMILES: Cc1ccc(CN2CC[C@@H](N3CC[C@@H](c4ccc(OP(=O)(O)O)cc4)[C@H](F)C3)C2=O)cc1]

To a suspension of (R)-3-((3S,4S)-3-fluoro-4-(4-hydroxyphenyl)piperidin-1-yl)-1-(4-methylbenzyl)pyrrolidin-2-one (100 mg, 0.261 mmol, example 1) in 10 mL of dichloromethane was added pyridine (0.106 mL, 1.31 mmol) and DMAP (160 mg, 1.31 mmol). The reaction mixture was chilled to −20° C. To the chilled solution was added POCl$_3$ (0.122 mL, 1.31 mmol) dropwise, and then the reaction mixture was allowed to warm to rt and stirred for 1 h. Water (10 mL) was added and the mixture was stirred for 1.5 h. The layers were then separated and the organic layer was dried over Na$_2$SO$_4$ and evaporated to dryness. The crude product was purified by HPLC on a Symmetry C8 (300×17 mm) 7 mM column eluting with a gradient of 20% B to 50% B over 7 minutes at 15 mL/min where solvent A=10 mM ammonium acetate in water pH 4.5 and solvent B=acetonitrile. The product RT=2.2 min. The desired product (5.8 mg, 4.7%) was isolated from the appropriate fractions by lyophilization as a white solid. LCMS (Conditions A) RT=1.720 min, (M+H)$^+$=463.2. $^1$H NMR (400 MHz, methanol-d4) δ 7.29-7.16 (m, 8H), 4.74 (br. s., 1H), 4.61-4.34 (m, 2H), 4.01 (t, J=8.3 Hz, 1H), 3.82-3.62 (m, 1H), 3.35 (m, 2H), 3.05 (br. s., 2H), 2.79 (br. s., 2H), 2.34 (s, 4H), 2.18 (br. s., 1H), 2.02-1.87 (m, 1H), 1.83 (br. s., 1H). $^{19}$F NMR (376 MHz, methanol-d4) δ −185.143. $^{31}$P NMR (162 MHz, methanol-d4) δ −4.260.

Example 3

(S)-4-((3S,4S)-3-Fluoro-1-((R)-1-(4-methylbenzyl)-2-oxopyrrolidin-3-yl)piperidin-4-yl)phenyl 2-amino-3-methylbutanoate hydrochloride

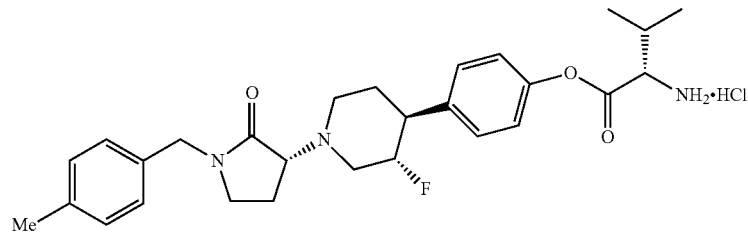

Step 3A. (S)-4-((3S,4S)-3-Fluoro-1-((R)-1-(4-methylbenzyl)-2-oxopyrrolidin-3-yl)piperidin-4-yl)phenyl 2-(((tert-butoxycarbonyl)amino)-3-methylbutanoate

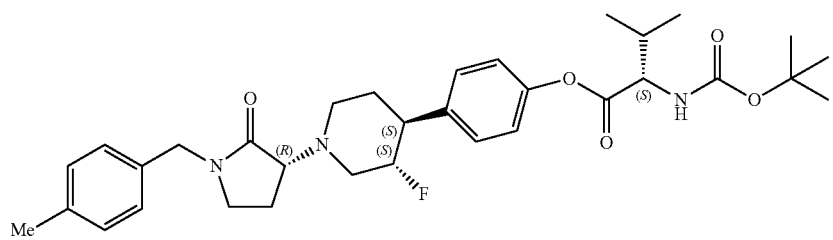

To a solution of (R)-3-((3S,4S)-3-fluoro-4-(4-hydroxyphenyl)piperidin-1-yl)-1-(4-methylbenzyl)pyrrolidin-2-one (0.02 g, 0.052 mmol, example 1) in DCM (3 mL) was added (S)-2-((tert-butoxycarbonyl)amino)-3-methylbutanoic acid (0.059 g, 0.272 mmol) followed by DCC (0.032 g, 0.157 mmol) and DMAP (6.39 mg, 0.052 mmol). The reaction mixture was stirred at room temperature for 18 h. Water (10 mL) was then added, and the layers were separated. The aqueous layer was extracted with DCM (3×10 mL) and the organic layers were combined, dried over $Na_2SO_4$, and concentrated to a crude product. The crude product was purified by preparative TLC eluting with 35% ethyl acetate in petroleum ether to provide the purified product (S)-4-((3S,4S)-3-fluoro-1-((R)-1-(4-methylbenzyl)-2-oxopyrrolidin-3-yl)piperidin-4-yl)phenyl 2-((tert-butoxycarbonyl)amino)-3-methylbutanoate (27 mg, 79%). LC/MS (Conditions A) RT=2.523 min, (M+H)$^+$=582.2. $^1$H NMR (400 MHz, methanol-d$_4$) δ 7.36 (d, J=8.5 Hz, 2H), 7.18 (s, 4H), 7.08 (d, J=8.5 Hz, 2H), 4.80-4.59 (m, J=10.0, 10.0, 5.0 Hz, 1H), 4.51 (d, J=15.0 Hz, 1H), 4.39 (d, J=15.0 Hz, 1H), 4.23 (dd, J=8.3, 6.3 Hz, 1H), 3.72 (t, J=8.8 Hz, 1H), 3.56-3.40 (m, 1H), 3.32-3.22 (m, 2H), 2.86-2.61 (m, 2H), 2.47 (td, J=10.0, 5.0 Hz, 1H), 2.34 (s, 3H), 2.32-2.23 (m, 1H), 2.22-2.01 (m, 2H), 1.88 (dd, J=9.5, 4.0 Hz, 2H), 1.74 (dt, J=13.4, 3.8 Hz, 1H), 1.50 (s, 9H), 1.42-1.30 (m, 1H), 1.09 (dd, J=10.0, 7.0 Hz, 6H). $^{19}$F NMR (376 MHz, methanol-d4) δ −184.32.

Step 3B. (S)-4-((3S,4S)-3-Fluoro-1-((R)-1-(4-methylbenzyl)-2-oxopyrrolidin-3-yl)piperidin-4-yl)phenyl 2-amino-3-methylbutanoate hydrochloride

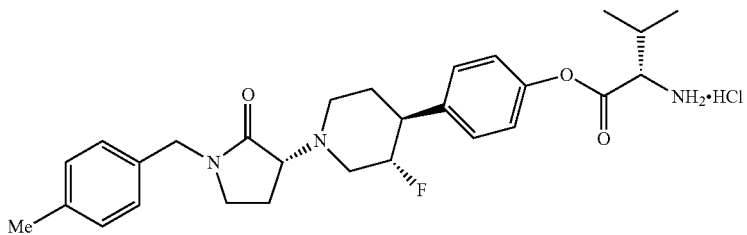

To a solution of (S)-4-((3S,4S)-3-fluoro-1-((R)-1-(4-methylbenzyl)-2-oxopyrrolidin-3-yl)piperidin-4-yl)phenyl 2-((tert-butoxycarbonyl)amino)-3-methylbutanoate (0.025 g, 0.043 mmol) in DCM (1.5 mL) at −20° C. was added HCl in diethyl ether (2.5 ml, 2.50 mmol, 1.0 M). The reaction mixture was slowly warmed to rt over 10 min and then allowed to stir at rt for 19 h. The solvent was then removed in vacuo to provide a pale yellow semisolid. The crude product was then purified by RP-HPLC on a Sunfire C18 (250×20 mm) 5 μm column using a gradient of 10% solvent B to 75% solvent B over 12 minutes at 15 mL/min where solvent A=0.05% HCl in water and solvent B=acetonitrile. Active fractions were concentrated by lyophilization to provide 10.2 mg (44%) of (S)-4-((3S,4S)-3-fluoro-1-((R)-1-(4-methylbenzyl)-2-oxopyrrolidin-3-yl)piperidin-4-yl)phenyl 2-amino-3-methylbutanoate hydrochloride, the titled compound of example 2 as an off-white solid. LC-MS (Method A) RT=2.20 min, (M+H)$^+$=482.2. $^1$H NMR: (400 MHz, DMSO-d6) δ ppm 8.64-8.78 (m, 3H) 7.38-7.46 (m, 2H) 7.23 (d, J=8.53 Hz, 2H) 7.18 (s, 4H) 5.04-5.26 (m, 1H) 4.42 (d, J=9.54 Hz, 3H) 4.17-4.23 (m, 2H) 3.29-3.40 (m, 4H) 3.19-3.28 (m, 2H) 2.30 (s, 6H) 2.04-2.19 (m, 2H) 1.11 (dd, J=12.55, 7.03 Hz, 6H). $^{19}$F NMR (376 MHz, DMSO-d6) δ −183.904.

Example 4

(S)-4-((3S,4S)-3-Fluoro-1-((R)-1-(4-methylbenzyl)-2-oxopyrrolidin-3-yl)piperidin-4-yl)phenyl 2-aminopropanoate hydrochloride

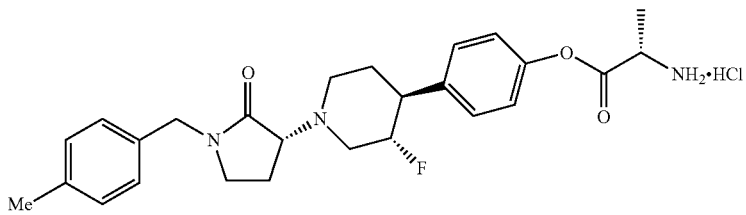

Step 4A. (S)-4-((3S,4S)-3-Fluoro-1-((R)-1-(4-methylbenzyl)-2-oxopyrrolidin-3-yl)piperidin-4-yl)phenyl 2-((tert-butoxycarbonyl)amino)propanoate

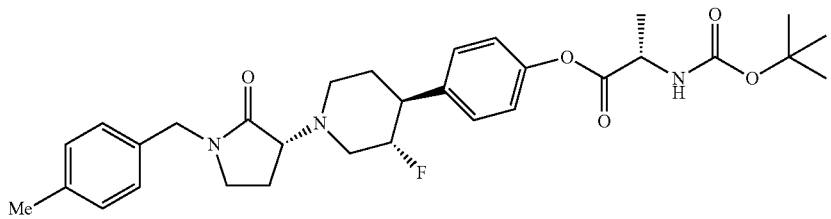 [SMILES: Cc1ccc(CN2CC[C@@H](N3CC[C@@H](c4ccc(OC(=O)[C@H](C)NC(=O)OC(C)(C)C)cc4)[C@H](F)C3)C2=O)cc1]

To a solution of (R)-3-((3S,4S)-3-fluoro-4-(4-hydroxyphenyl)piperidin-1-yl)-1-(4-methylbenzyl)pyrrolidin-2-one (0.03 g, 0.078 mmol, example 1) in DCM (5 mL) was added (S)-2-((tert-butoxycarbonyl)amino)propanoic acid (0.077 g, 0.408 mmol) followed by DCC (0.049 g, 0.235 mmol) and DMAP (9.58 mg, 0.078 mmol). The reaction mixture was stirred at rt for 18 h. Water (15 mL) was then added, and the layers were separated. The aqueous layer was extracted with DCM (3×15 mL) and the organic layers were combined, dried over $Na_2SO_4$, and concentrated to a crude product. The crude product was purified by preparative TLC eluting with 20% ethyl acetate in petroleum ether to provide the purified product (S)-4-((3S,4S)-3-fluoro-1-((R)-1-(4-methylbenzyl)-2-oxopyrrolidin-3-yl)piperidin-4-yl)phenyl 2-((tert-butoxycarbonyl)amino)propanoate (0.032 g, 0.058 mmol, 74% yield) as off-white semi solid. LC-MS (Method A) RT=2.40 min, (M+H)$^+$=554.2. $^1$H NMR (400 MHz, DMSO-$d_6$) δ 7.51 (d, J=7.0 Hz, 1H), 7.44-7.32 (m, J=8.5 Hz, 2H), 7.21-7.09 (m, 4H), 7.07-6.98 (m, J=8.5 Hz, 2H), 4.62 (d, J=4.5 Hz, 1H), 4.39 (d, J=15.1 Hz, 1H), 4.30 (d, J=15.1 Hz, 1H), 4.27-4.17 (m, 1H), 3.58 (t, J=8.5 Hz, 1H), 3.50-3.40 (m, 1H), 3.22-3.07 (m, 2H), 2.81-2.64 (m, 3H), 2.39-2.31 (m, 1H), 2.29 (s, 3H), 2.17-2.04 (m, 1H), 1.93 (dd, J=12.8, 8.3 Hz, 1H), 1.78 (br. s., 1H), 1.74-1.59 (m, 1H), 1.41 (s, 9H), 1.39 (d, J=2.5 Hz, 3H). $^{19}$F NMR (376 MHz, DMSO-d6) δ −180.172.

Step 4B. (S)-4-((3S,4S)-3-Fluoro-1-((R)-1-(4-methylbenzyl)-2-oxopyrrolidin-3-yl)piperidin-4-yl)phenyl 2-aminopropanoate hydrochloride To a solution of (S)-4-((3S,4S)-3-fluoro-1-((R)-1-(4-methylbenzyl)-2-oxopyrrolidin-3-yl)piperidin-4-yl)phenyl 2-((tert-butoxycarbonyl)amino)propanoate (0.032 g, 0.058 mmol) in DCM (2 mL) at −20° C. was added HCl in diethyl ether (2.0 ml, 2.0 mmol, 1.0 M). The reaction mixture was slowly warmed to rt over 10 min and then allowed to stir at rt for 19 h. The solvent was then removed in vacuo to provide a pale yellow semisolid. The crude product was then purified by RP-HPLC on a Kinetex C18 (250×20 mm) 5 μm column using a gradient of 10% solvent B to 40% solvent B over 7 minutes at 15 mL/min where solvent A=0.05% HCl in water and solvent B=acetonitrile. Active fractions were concentrated by lyophilization to provide 4.7 mg (16%) of (S)-4-((3S,4S)-3-fluoro-1-((R)-1-(4-methylbenzyl)-2-oxopyrrolidin-3-yl)piperidin-4-yl)phenyl 2-aminopropanoate hydrochloride, the titled compound of example 4 as an off-white solid. LC-MS (Method A) RT=1.762 min, (M+H)$^+$=454. $^1$H NMR (400 MHz, DMSO-$d_6$) δ 7.41 (d, J=9.0 Hz, 2H), 7.24-7.10 (m, 6H), 5.10-4.85 (m, 1H), 4.45-4.22 (m, 4H), 4.04-3.94 (m, 1H), 3.34-3.18 (m, 4H), 3.06 (d, J=12.0 Hz, 2H), 2.43-2.31 (m, 1H), 2.27 (s, 3H), 2.24-2.14 (m, 1H), 2.13-2.01 (m, 1H), 2.01-1.85 (m, 1H), 1.58 (d, J=7.0 Hz, 3H). $^{19}$F NMR (376 MHz, DMSO-d6) δ −183.778.

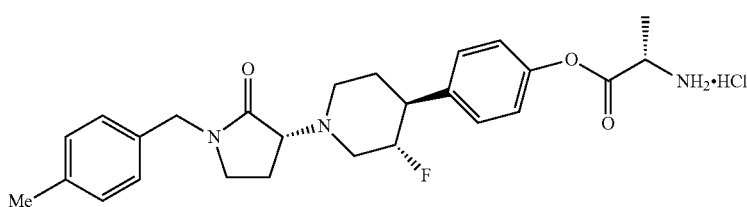

Example 5

(S)-2-Amino-4-(4-((3S,4S)-3-fluoro-1-((R)-1-(4-methylbenzyl)-2-oxopyrrolidin-3-yl)piperidin-4-yl)phenoxy)-4-oxobutanoic acid hydrochloride

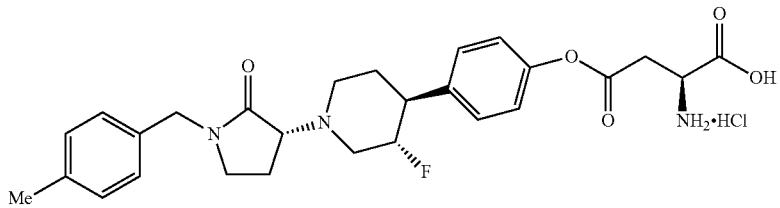

Step 5A. (S)-1-tert-Butyl 4-(4-((3S,4S)-3-fluoro-1-((R)-1-(4-methylbenzyl)-2-oxopyrrolidin-3-yl)piperidin-4-yl)phenyl) 2-((tert-butoxycarbonyl)amino)succinate

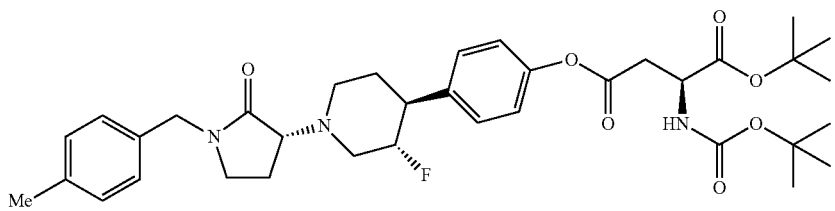 [SMILES: Cc1ccc(CN2CC[C@@H](N3CC[C@@H](c4ccc(OC(=O)C[C@H](NC(=O)OC(C)(C)C)C(=O)OC(C)(C)C)cc4)[C@H](F)C3)C2=O)cc1]

To a solution of (R)-3-((3S,4S)-3-fluoro-4-(4-hydroxyphenyl)piperidin-1-yl)-1-(4-methylbenzyl)pyrrolidin-2-one (0.03 g, 0.078 mmol) in DCM (5 mL) was added (S)-4-(tert-butoxy)-3-((tert-butoxycarbonyl)amino)-4-oxobutanoic acid (0.118 g, 0.408 mmol) followed by DCC (0.049 g, 0.235 mmol) and DMAP (9.58 mg, 0.078 mmol). The reaction was stirred at rt for 18 hours. Water (15 mL) was then added, and the layers were separated. The aqueous layer was extracted with DCM (3×15 mL) and the organic layers were combined, dried over Na$_2$SO$_4$, and concentrated to a crude product. The crude product was purified by preparative TLC eluting with 25% ethyl acetate in petroleum ether to provide the purified product (37 mg, 68%) as an off-white semi solid. LC-MS (Method A) RT=2.55 min, (M+H)$^+$ =654.4. $^1$H NMR (400 MHz, DMSO-d$_6$) δ 7.46-7.34 (m, 2H), 7.20-6.98 (m, 6H), 4.82-4.53 (m, 1H), 4.43-4.24 (m, 2H), 4.11 (d, J=14.1 Hz, 1H), 3.58 (t, J=8.8 Hz, 1H), 3.48-3.39 (m, 1H), 3.22-3.07 (m, 3H), 3.02 (dd, J=16.1, 6.5 Hz, 1H), 2.87 (dd, J=15.8, 7.8 Hz, 1H), 2.78-2.63 (m, 2H), 2.38-2.31 (m, 1H), 2.29 (s, 3H), 2.17-2.03 (m, 1H), 1.98-1.86 (m, 1H), 1.78 (br. s., 1H), 1.74-1.58 (m, 1H), 1.42 (s, 9H), 1.39 (s, 9H). $^{19}$F NMR (376 MHz, DMSO-d6) δ −180.707.

Step 5B. (S)-2-amino-4-(4-((3S,4S)-3-fluoro-1-((R)-1-(4-methylbenzyl)-2-oxopyrrolidin-3-yl)piperidin-4-yl)phenoxy)-4-oxobutanoic acid hydrochloride

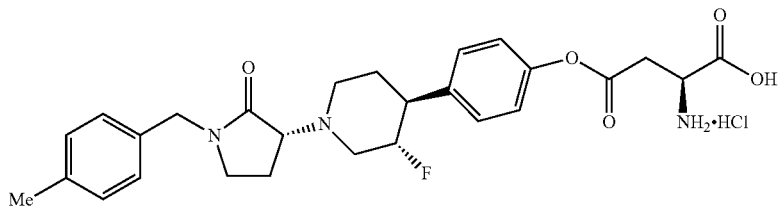

To a solution of (S)-1-tert-butyl 4-(4-((3S,4S)-3-fluoro-1-((R)-1-(4-methylbenzyl)-2-oxopyrrolidin-3-yl)piperidin-4-yl)phenyl) 2-((tert-butoxycarbonyl)amino)succinate (0.032 g, 0.049 mmol) in DCM (2 mL) at −20° C. was added HCl in diethyl ether (2.0 ml, 2.0 mmol, 1.0 M). The reaction mixture was slowly warmed to rt over 10 min and then allowed to stir at rt for 19 h. The solvent was then removed in vacuo to provide a pale yellow semisolid. The crude product was then purified by RP-HPLC on a YMC Triart C18 (150×19 mm) 5 μm column using a gradient of 10% solvent B to 40% solvent B over 7 minutes at 15 mL/min where solvent A=0.05% HCl in water and solvent B=acetonitrile. Active fractions were concentrated by lyophilization to provide 17 mg (57%) of (S)-2-amino-4-(4-((3S,4S)-3-fluoro-1-((R)-1-(4-methylbenzyl)-2-oxopyrrolidin-3-yl)piperidin-4-yl)phenoxy)-4-oxobutanoic acid hydrochloride, the titled compound of example 5 as an off-white solid. LC-MS (Method A) RT=1.808 min, (M+H)+=498.2 $^1$H NMR (400 MHz, DMSO-d$_6$) δ 7.36 (d, J=8.5 Hz, 2H), 7.21-7.03 (m, 8H), 6.75 (d, J=8.5 Hz, 1H), 4.95-4.72 (m, 1H), 4.42-4.24 (m, 3H), 4.10 (t, J=5.3 Hz, 1H), 4.07-4.01 (m, 1H), 3.93-3.84 (m, 1H), 3.83-3.68 (m, 1H), 3.33-3.10 (m, 5H), 3.04 (br. s., 1H), 2.93 (br. s., 1H), 2.89-2.71 (m, 2H), 2.26 (s, 3H), 1.96 (br. s., 1H), 1.82 (br. s., 1H). $^{19}$F NMR (376 MHz, DMSO-d6) δ −180.707.

Example 6

(R)-1-(4-(Difluoromethyl)benzyl)-3-((3S,4S)-3-fluoro-4-(4-hydroxyphenyl)piperidin-1-yl)pyrrolidin-2-one

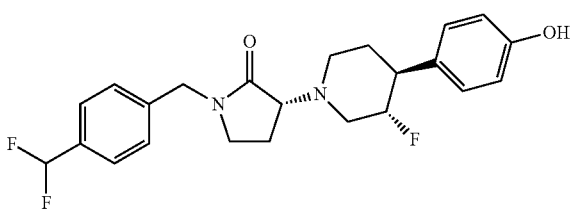 [SMILES: O=C1[C@H](N2CC[C@@H](c3ccc(O)cc3)[C@H](F)C2)CCN1Cc1ccc(C(F)F)cc1]

A solution of (S)-1-(4-(difluoromethyl)benzyl)-2-oxopyrrolidin-3-yl methanesulfonate (500 mg, 1.57 mmol, intermediate M) in 5.0 mL of acetonitrile was added dropwise over 1.5 h to a stirred mixture of 4-((3S,4S)-3-fluoropiperidin-4-yl)phenol, hydrochloride (363 mg, 1.57 mmol, intermediate F) and N,N-diisopropylethylamine (1.09 mL, 6.26 mmol) in 5.0 mL of acetonitrile maintained at 85° C. After complete addition, the reaction mixture was stirred at 85° C. for 16 h. The reaction mixture was concentrated in vacuo. The residue was purified using silica gel column chromatography (0-100% EtOAc/hexanes) to afford a diasteromeric mixture (partial epimerization of the lactam stereocenter) of 1-(4-(difluoromethyl)benzyl)-3-((3S,4S)-3-fluoro-4-(4-hydroxyphenyl)piperidin-1-yl)pyrrolidin-2-one (235 mg, 35% yield). A sample of the diastereomeric mixture (780 mg) was separated by preparative chiral SFC (column=Lux Cellulose-2 (21×250 mm, 5 μm); isocratic solvent=20% methanol (with 15 mM ammonia)/80% CO$_2$; temp=35° C.; flow rate=60 mL/min; injection volumn=1.0 mL (~20 mg/mL in MeOH) stacked @ 13 min intervals; λ=210 nM; Peak 1=19.6 min, Peak 2=24.5 min) to afford the titled compounds of example 6 (Peak-1, 389 mg) and (S)-1-(4-(difluoromethyl)benzyl)-3-((3S,4S)-3-fluoro-4-(4-hydroxyphenyl)piperidin-1-yl)pyrrolidin-2-one (Peak 2, 242 mg). Data for Example 6: LC-MS m/z 419.3 (M+H); $^1$H NMR (500 MHz, chloroform-d) δ 7.50 (d, J=7.9 Hz, 2H), 7.34 (d, J=7.9 Hz, 2H), 7.15 (d, J=8.5 Hz, 2H), 6.91-6.80 (m, 2H), 6.65 (t, J=56.4 Hz, 1H), 4.96 (s, 1H), 4.77-4.43 (m, 3H), 3.68 (t, J=8.8 Hz, 1H), 3.42-3.33 (m, 1H), 3.29-3.14 (m, 2H), 2.85 (d, J=10.4 Hz, 1H), 2.78-2.69 (m, 1H), 2.69-2.57 (m, 1H), 2.48 (td, J=9.9, 4.9 Hz, 1H), 2.21-2.11 (m, 1H), 2.04 (dq, J=13.0, 8.6 Hz, 1H), 1.94-1.82 (m, 2H)). The relative and absolute configuration of Example 114, P-1 was confirmed by single crystal X-ray analysis.

Example 7

4-((3S,4S)-fluoro-1-((R)-1-(4-methylbenzyl)-2-oxopyrrolidin-3-yl)piperidin-4-yl)phenyl dihydrogen phosphate

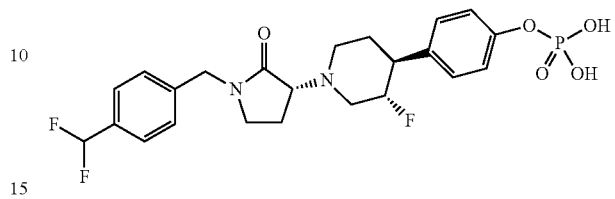

To a suspension of (R)-1-(4-(difluoromethyl)benzyl)-3-((3S,4S)-3-fluoro-4-(4-hydroxyphenyl)piperidin-1-yl)pyrrolidin-2-one (100 mg, 0.239 mmol, from example 6) in dichloromethane (10 mL) was added triethylamine (0.233 ml, 1.67 mmol) at −20° C. To the chilled solution was added POCl$_3$ (0.111 ml, 1.20 mmol) at −20° C., and then the reaction mixture was stirred for 2-3 hours at −20° C. Water (10 mL) was added and the mixture was stirred for 1.5 h. The mixture was extracted with dichloromethane. The organic layers was dried over sodium sulfate, filtered, and concentrated in vacuo. The crude product was purified by reverse phase preparatory HPLC on a LUNA C8 (250 mm×19 mm ID) 5 μm column eluting with a gradient of solvent A=10 mM ammonium acetate in water pH 4.5 and solvent B=acetonitrile. The titled compound of example 7 (21 mg, 18%) was isolated from the appropriate fractions by lyophilization as a white solid. LCMS (M+H)+=499.2; $^1$H NMR (400 MHz, METHANOL-d4) δ ppm 7.55 (d, J=8.03 Hz, 2H) 7.41 (d, J=8.03 Hz, 2H) 7.21 (s, 4H) 6.62-6.92 (m, 1H) 4.51-4.64 (m, 3H) 3.76 (t, J=8.78 Hz, 1H) 3.43-3.51 (m, 1H) 3.36 (d, J=6.02 Hz, 1H) 3.26-3.30 (m, 1H) 2.81 (br. s., 1H) 2.70-2.78 (m, 1H) 2.59-2.69 (m, 1H) 2.48 (td, J=9.91, 4.77 Hz, 1H) 2.17-2.27 (m, 1H) 2.06-2.15 (m, 1H) 1.80-1.89 (m, 2H).

Example 8

(R)-1-(4-Fluorobenzyl)-3-(4-(4-hydroxyphenyl)piperidin-1-yl)pyrrolidin-2-one

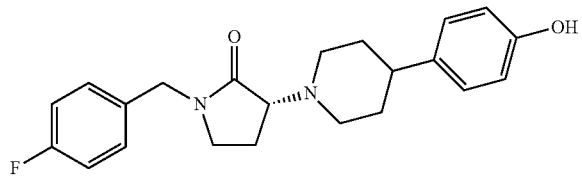 [SMILES: O=C1[C@H](N2CCC(c3ccc(O)cc3)CC2)CCN1Cc1ccc(F)cc1]

To a solution of 1-(4-fluorobenzyl)-3-(4-(4-methoxyphenyl)piperidin-1-yl)pyrrolidin-2-one (3 g, 7.9 mmol, intermediate S) in dry dichloromethane (100 mL) under a N$_2$ atmosphere at −78° C. was added 1 M borontribromide in dichloromethane (39 mL, 39 mmol) and the resulting mixture was allowed to warm up to room temperature over 3 h, with stirring. The reaction was quenched with water (30 mL) and the organic layer was separated, washed with water and brine, and concentrated. The crude product was purified by flash chromatography on silica gel using 15% EtOAc in petroleum ether to yield racemic 1-(4-fluorobenzyl)-3-(4-(4-hydroxyphenyl)piperidin-1-yl)pyrrolidin-2-one (2.1 g, 73% yield); $^1$H NMR (400 MHz, DMSO-$d_6$) δ ppm 1.49-1.74 (m, 4H) 1.90-2.11 (m, 2H) 2.24-2.42 (m, 2H) 2.65-2.80 (m, 2H) 2.99-3.23 (m, 3H) 3.40-3.54 (m, 1H) 4.27-4.46 (m, 2H) 6.61-6.70 (m, 2H) 6.95-7.04 (m, 2H) 7.17-7.31 (m, 4H) 9.10-9.16 (m, 1H). LCMS (ES-API) 369.2 m/z (M+H)$^+$. A portion of the racemate (40 mg) was separated via SFC on a Chiralpak-IA 250 mm×4.6 mm, 5 μm column eluting with 35% solvent B, where solvent A=$CO_2$ and solvent B=0.3% DEA in methanol at a total flow of 3 mL/min. Peak 1 showed a RT of 4.35 min (11 mg) and Peak 2 showed a RT of 6.29 min (13 mg). Data for example 8 (Peak 2): LC/MS (M+H)$^+$=369.2; $^1$H NMR (400 MHz, DMSO-$d_6$) δ ppm 1.47-1.59 (m, 1H) 1.65-1.75 (m, 1H) 1.84-1.96 (m, 1H) 2.03-2.12 (m, 1H) 2.24-2.43 (m, 1H) 2.63-2.72 (m, 2H) 2.72-2.85 (m, 2H) 2.96-3.05 (m, 2H) 3.09-3.23 (m, 2H) 3.41-3.54 (m, 1H) 4.23-4.50 (m, 2H) 6.58-6.71 (m, 2H) 6.96-7.10 (m, 2H) 7.15-7.21 (m, 2H) 7.26-7.34 (m, 2H) 9.06-9.19 (m, 1H).

Example 9

(R)-4-(1-(1-(4-fluorobenzyl)-2-oxopyrrolidin-3-yl)piperidin-4-yl)phenyl dihydrogen phosphate

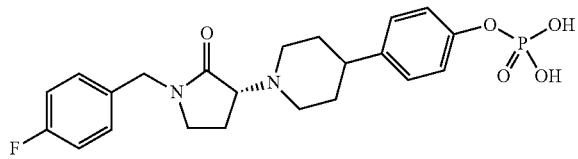 [SMILES: O=C1[C@H](N2CCC(c3ccc(OP(=O)(O)O)cc3)CC2)CCN1Cc1ccc(F)cc1]

Phosphorus oxychloride (1.27 mL, 13.6 mmol) was added to a round bottom flask charged with THF (10 mL). The solution was cooled below 0° C. using an ice/methanol bath. A suspension of (R)-1-(4-fluorobenzyl)-3-(4-(4-hydroxyphenyl)piperidin-1-yl)pyrrolidin-2-one (1.00 g, 2.71 mmol, example 8) in THF (18 mL) was added. After 5 min, triethylamine (0.946 mL, 6.79 mmol) was added slowly at a bath temperature below 5° C. The reaction mixture was stirred at 0° C. for 90 min. A solution of 1 N aqueous sodium hydroxide (8.69 mL, 8.69 mmol) was added dropwise. The pH was measured to be ~0. The mixture was allowed to warm to rt and stir for 3 h. The crude reaction mixture was concentrated in vacuo at <30° C. to afford a clear solution. The solution was triturated with 1 N aqueous NaOH to pH ~1. The mixture was cooled in an ice bath. A semi-solid crashed out. All liquid was decanted off. The semi-solid was suspended in 90% ethanol and then a collected by vacuum filtration. The product was presumed to be the HCl salt of (R)-4-(1-(1-(4-fluorobenzyl)-2-oxopyrrolidin-3-yl)piperidin-4-yl)phenyl dihydrogen phosphate (560 mg, 42%). A solution of 25% sodium methoxide in methanol (250 mg, 1.16 mmol) was added to a slurry of (R)-4-(1-(1-(4-fluorobenzyl)-2-oxopyrrolidin-3-yl)piperidin-4-yl)phenyl dihydrogen phosphate, HCl (560 mg, 1.16 mmol) in methanol. The mixture was stirred until clear and then concentrated in vacuo. The residue was dissolved in 90% ethanol/water and chilled in the freezer.

The solid precipitate was collected using vacuum filtration. The solid was dried under high vacuum to afford the titled compound of example 9 (230 mg, 19% yield): LC/MS (M+H)$^+$=449.2; $^1$H NMR (500 MHz, methanol-$d_4$) δ 7.35-7.25 (m, 2H), 7.21-7.11 (m, 4H), 7.11-7.03 (m, 2H), 4.55-4.35 (m, 2H), 3.61 (t, J=8.8 Hz, 1H), 3.30-3.20 (m, 2H), 3.19-3.11 (m, 1H), 2.92-2.84 (m, 1H), 2.75 (td, J=11.1, 3.5 Hz, 1H), 2.55-2.41 (m, 2H), 2.23-2.13 (m, 1H), 2.12-2.00 (m, 1H), 1.84-1.70 (m, 4H); $^{31}$P NMR (202 MHz, methanol-$d_4$) δ ppm −3.38.

Biological Methods

Radioligand Binding Assay.

Binding experiments to determine binding to NR2B-subtype NMDA receptors were performed on forebrains of 8-10 weeks old male Sprague Dawley rats (Harlan, Netherlands) using $^3$H Ro 25-6981 (Mutel V; Buchy D; Klingelschmidt A; Messer J; Bleuel Z; Kemp J A; Richards J G. *Journal of Neurochemistry*, 1998, 70(5):2147-2155. Rats were decapitated without anesthesia using a Guillotine (approved by animal ethics committee) and the harvested brains were snap-frozen and stored at −80° C. for 3-6 months for membrane preparation.

For membrane preparation, rat forebrains were thawed on ice for 20 minutes in homogenization buffer composed of 50 mM $KH_2PO_4$ (pH adjusted to 7.4 with KOH), 1 mM EDTA, 0.005% Triton X 100 and protease inhibitor cocktail (Sigma Aldrich). Thawed brains were homogenized using a Dounce homogenizer and centrifuged at 48000×g for 20 min. The pellet was resuspended in cold buffer and homogenized again using a Dounce homogenizer. Subsequently, the homogenate was aliquoted, snap-frozen and stored at −80° C. for not more than 3-4 months.

To perform the competition binding assay, thawed membrane homogenate was added to each well of a 96-well plate (20 μg/well). The experimental compounds were serially diluted in 100% DMSO and added to each row of the assay plate to achieve desired compound concentrations, keeping the DMSO concentration in the assay plate at 1.33% of the final reaction volume. Next, $^3$H Ro 25-6981 (4 nM) was added to the assay plate. After incubation for 1 hr at room temperature, the membrane bound radioligand was harvested on to GF/B filter plates (treated with 0.5% PEI for 1 hr at room temperature). The filter plates were dried at 50° C. for 20 mins, incubated with microscint 20 for 10 minutes and finally, the counts were read on TopCount (Perkin Elmer). Non-specific binding was determined using MK-0657 (the preparation of this compound is described as example 1 in WO 2004 108705 (40 μM). CPM values were converted to % inhibition and the concentration response curves were plotted using custom made software. Each experiment was repeated at least twice to obtain the final binding $K_i$ values for experimental compounds. Using this assay, the compound of example 1 showed a binding Ki of 4 nM, the compound of example 6 showed a binding Ki of 4 nM, the compound of example 8 showed a binding Ki of 1.4 nM.

Ex Vivo Occupancy Assay.

This assay demonstrates that the compound of example 1 occupies brain-resident NR2B-subtype receptors in animals after dosing. 7-9 weeks old male CD-1 mice were dosed intravenously in a vehicle consisting of 10% dimethylacetamide, 40% PEG-400, 30% hydroxypropyl betacyclodextrin, and 30% water with experimental compounds and the forebrains were harvested 15 minutes post-dosing by decapitation. The brain samples were immediately snap-frozen and stored at −80° C. On the following day, the dosed brain samples were thawed on ice for 15-20 minutes followed by homogenization using Polytron for 10 seconds in cold homogenization buffer composed of 50 mM $KH_2PO_4$ (pH adjusted to 7.4 with KOH), 1 mM EDTA, 0.005% Triton X 100 and protease inhibitor cocktail (Sigma Aldrich). The crude homogenates were further homogenized using a Dounce homogenizer and the homogenized membrane aliquots from all animals were flash-frozen and stored at −80° C. until further use. The whole homogenization process was performed on ice.

For determining occupancy, the membrane homogenates were first thawed on ice and then needle-homogenized using a 25 gauge needle. The homogenized membrane (6.4 mg/ml) was added to a 96-well plate followed by addition of $^3$H Ro 25-6981 (6 nM). The reaction mixture was incubated for 5 minutes on a shaker at 4° C. and then harvested onto GF/B filter plates (treated with 0.5% PEI for 1 hr at room temperature). The filter plates were dried at 50° C. for 20 mins, incubated with microscint 20 for 10 minutes and read on TopCount (Perkin Elmer). Each dose or compound group consisted of 4-5 animals. The control group of animals was dosed with vehicle alone. Membrane from each animal was added in triplicates to the assay plate. Non-specific binding was determined using 10 μM Ro 25-6981 added to the wells containing membrane homogenates from vehicle-dosed animals. Specific counts/minute was converted to % occupancy at each dose of a compound for each animal using the following equation:

$$\% \text{ Occupancy (animal } A) = 100 - \left( \frac{\text{specific } CPM \text{ of animal } A}{\text{Average } CPM \text{ from control group}} \times 100 \right)$$

Using this procedure, the compound of example 1 showed 95% NR2B receptor occupancy after a 3 mg/Kg i.v. dose. Drug levels were determined by mass spectroscopy in the usual manner. Drug levels in the blood plasma were 1106 nM in at this dose, and drug levels in the homogonized brain tissue were 1984 nM. The compound of example 6 showed 97% NR2B receptor occupancy after a 3 mg/Kg i.v. dose. Drug levels in the blood plasma were 1800 nM in at this dose, and drug levels in the homogonized brain tissue were 2200 nM. The compound of example 8 showed 96% NR2B receptor occupancy after a 3 mg/Kg i.v. dose. Drug levels in the blood plasma were 570 nM at this dose, and drug levels in the homogonized brain tissue were 900 nM.

hERG Electrophysiology Assay.

The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 CaCl$_2$, 1 MgCl$_2$, 10 Glucose, 10 HEPES (pH 7.4, NaOH) at room temperature. Borosilicate patch pipettes had tip resistances of 2-4 Mohms when filled with an internal solution containing 130 KCl, 1 MgCl$_2$, 1 CaCl$_2$, 10 EGTA, 10 HEPES, 5 ATP-K$_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents and then, back to the holding potential. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in custom made software. The percent inhibitions at different concentrations were plotted to obtain a concentration response curve, which was subsequently fitted with a four parameter equation to calculate the hERG IC$_{50}$ value. Using this procedure, the compound of example 1 is a poor inhibitor of the hERG channel, with an IC$_{50}$=28 μM. The compound of example 6 is a poor inhibitor of the hERG channel, with an IC$_{50}$=13.5 μM.

Mouse Forced Swim Test (mFST).

Forced Swim Test (FST) is an animal model used to assess antidepressant compounds in preclinical studies. The FST was performed similar to the method of Porsolt et al. with modifications (Porsolt R D, Bertin A, Jalfre M. Behavioral despair in mice: a primary screening test for antidepressants. Arch Int Pharmacodyn Thér 1977; 229:327-36). In this paradigm, mice are forced to swim in an inescapable cylinder filled with water. Under these conditions, mice will initially try to escape and eventually develop immobility behavior; this behavior is interpreted as a passive stress-coping strategy or depression-like behavior. Swim tanks were positioned inside a box made of plastic. Each tank was separated from each other by opaque plastic sheets to the height of cylinders. Three mice were subjected to test at a time. Swim sessions were conducted for 6 min by placing mice in individual glass cylinders (46 cm height×20 cm diameter) containing water (20-cm deep, maintained at 24-25° C.). At this water level, the mouse tail does not touch the bottom of the container. The mouse was judged to be immobile whenever it remained floating passively without struggling in the water and only making those movements necessary to keep its nose/head above the water and to keep it afloat. The duration of immobility was evaluated during the total 6 min of the test and expressed as duration (sec) of immobility. Each mouse was tested only once. At the end of each session, mice were dried with a dry cloth and returned to their home cage placed on a thermal blanket to prevent hypothermia. Water was replaced after each trial. All testing sessions were recorded with a video camera (Sony Handicam, Model: DCR-HC38E; PAL) and scoring was done using the Forced Swim Scan, Version 2.0 software (Clever Systems Inc., Reston, Va., USA; see Hayashi E, Shimamura M, Kuratani K, Kinoshita M, Hara H. Automated experimental system capturing three behavioral components during murine forced swim test. Life Sci. 2011 Feb. 28; 88(9-10):411-7 and Yuan P, Tragon T, Xia M, Leclair C A, Skoumbourdis A P, Zheng W, Thomas C J, Huang R, Austin C P, Chen G, Guitart X. Phosphodiesterase 4 inhibitors enhance sexual pleasure-seeking activity in rodents. Pharmacol Biochem Behav. 2011; 98(3):349-55). For NCE testing: Test compound was administered in mice 15 min before swim session by i.v. route and immobility time was recorded for next 6 min. At the end of FST, the mouse were euthanized by rapid decapitation method and plasma and brain samples were collected and stored under −80° C. till further analysis. In the mouse forced swim assay, the compound of example 1 was dosed intraveneously in a vehicle of 30% hydroxypropyl betacyclodextrin/70% citrate buffer pH 4 at a 5 mL/Kg dosing volume. The compound of example 1 demonstrated a statistically significant decrease in immobility time at 1 mg/Kg under these conditions. Drug levels were 268+/−128 nM in the plasma and 749+/−215 nM in the brain at this dose. The NR2B receptor occupancy was determined as reported above and was determined to be 73%. The compound of example 6 demonstrated a statistically significant decrease in immobility time at 1 mg/Kg under these same conditions. Drug levels were 360 nM in the plasma. The NR2B receptor occupancy was determined to be 79%.

We claim:
1. A compound of the formula I

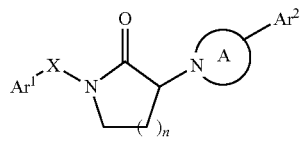

where:
Ar[1] is phenyl or indanyl and is substituted with 0-3 substituents selected from cyano, halo, alkyl, haloalkyl, and haloalkoxy;
Ar[2] is phenyl substituted with 1 OR substituent and also substituted with 0-3 substituents selected from cyano, halo, alkyl, haloalkyl, and haloalkoxy;
R is a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2; and
ring A is azetidinyl, pyrrolidinyl, piperidinyl, piperazinyl, homopiperidinyl, or homopiperazinyl and is substituted with 0-4 substituents selected from halo, alkyl, hydroxy, or alkoxy;
or a pharmaceutically acceptable salt thereof.

2. A compound of claim 1 with the formula

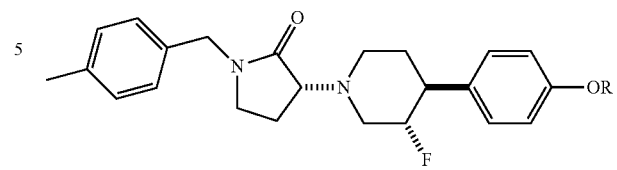

where R is a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates; or a pharmaceutically acceptable salt thereof.

3. The compound of claim 2: 4-((3S,4S)-3-fluoro-1-((R)-1-(4-methylbenzyl)-2-oxopyrrolidin-3-yl)piperidin-4-yl)phenyl dihydrogen phosphate, or a pharmaceutically acceptable salt thereof

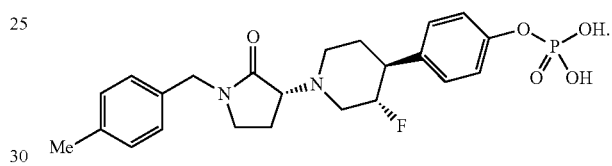

4. The compound of claim 2: (S)-4-((3S,4S)-3-fluoro-1-((R)-1-(4-methylbenzyl)-2-oxopyrrolidin-3-yl)piperidin-4-yl)phenyl 2-amino-3-methylbutanoate hydrochloride, or a pharmaceutically acceptable salt thereof

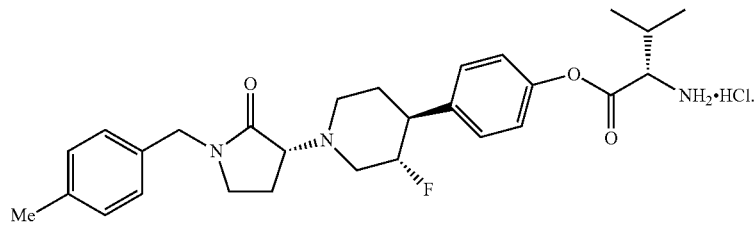

5. The compound of claim 2: (S)-4-((3S,4S)-3-fluoro-1-((R)-1-(4-methylbenzyl)-2-oxopyrrolidin-3-yl)piperidin-4-yl)phenyl 2-aminopropanoate hydrochloride, or a pharmaceutically acceptable salt thereof;

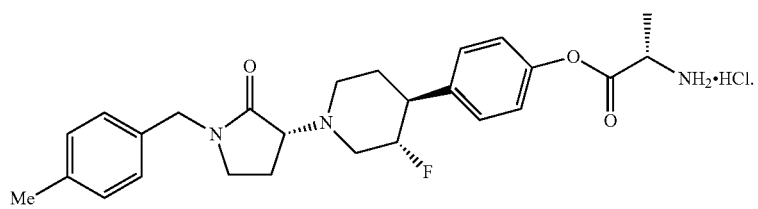

6. The compound of claim 2: (S)-2-amino-4-(4-((3S,4S)-3-fluoro-1-((R)-1-(4-methylbenzyl)-2-oxopyrrolidin-3-yl)piperidin-4-yl)phenoxy)-4-oxobutanoic acid hydrochloride, or a pharmaceutically acceptable salt thereof;

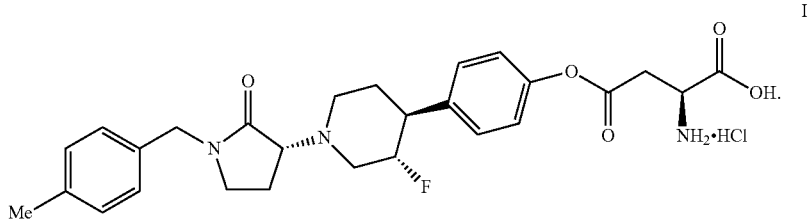

7. The compound of claim 1: 4-((3S,4S)-3-fluoro-1-((R)-1-(4-methylbenzyl)-2-oxopyrrolidin-3-yl)piperidin-4-yl)phenyl dihydrogen phosphate, or a pharmaceutically acceptable salt thereof;

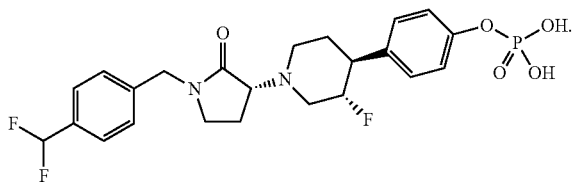 [SMILES: O=C1[C@H](N2CC[C@@H](c3ccc(OP(=O)(O)O)cc3)[C@H](F)C2)CCN1Cc1ccc(C(F)F)cc1]

8. A pharmaceutical composition comprising a compound of claim 1 or a pharmaceutically acceptable salt thereof and a pharmaceutically acceptable carrier.

9. A method for the treatment of depression, Alzheimer's disease, neuropathic pain, or Parkinson's disease, which comprises administering to a patient a therapeutically affective amount of a compound of claim 1.

10. The method of claim 9 directed to the treatment of depression.

11. The method of claim 9 directed to the treatment of Alzheimer's disease.

12. The method of claim 9 directed to the treatment of neuropathic pain.

* * * * *